United States Patent [19]
Clerc

[11] Patent Number: 6,144,023
[45] Date of Patent: Nov. 7, 2000

[54] ELECTRODE SUPPORT COMPRISING AT LEAST ONE ELECTRODE COVERED BY A DEPOSIT AND SYSTEM FOR READING THIS SUPPORT

[75] Inventor: Jean-Frédéric Clerc, Le Fontanil, France

[73] Assignee: Commissariat a l'Energie Atomique, Paris, France

[21] Appl. No.: 09/089,101

[22] Filed: Jun. 2, 1998

[30] Foreign Application Priority Data

Jun. 6, 1997 [FR] France ................................. 97 07048

[51] Int. Cl.[7] ..................................................... G01J 1/42
[52] U.S. Cl. ..................................... 250/208.2; 435/286.1
[58] Field of Search ...................... 250/208.2; 435/286.1, 435/287.3, 287.9, 288.7, 292.1, 808, 6; 204/461, 612

[56] References Cited

U.S. PATENT DOCUMENTS

| | | |
|---|---|---|
| 3,230,163 | 1/1966 | Dreyfus . |
| 3,878,061 | 4/1975 | Feldstein . |
| 4,139,348 | 2/1979 | Swartz ...................................... 436/35 |
| 4,676,761 | 6/1987 | Poujois ....................................... 445/3 |
| 4,803,049 | 2/1989 | Hirschfeld et al. ........................ 422/58 |
| 5,008,617 | 4/1991 | Czubatyj et al. ................... 324/158 R |
| 5,103,557 | 4/1992 | Leedy ....................................... 29/832 |
| 5,120,421 | 6/1992 | Glass et al. ............................. 204/406 |
| 5,135,606 | 8/1992 | Kato et al. . |

(List continued on next page.)

FOREIGN PATENT DOCUMENTS

| | | |
|---|---|---|
| 0239969 | 10/1987 | European Pat. Off. ..... G01N 33/545 |
| 0421406 | 4/1991 | European Pat. Off. ....... G01N 15/14 |
| 1013183 | 1/1989 | Japan . |
| 1179995 | 7/1989 | Japan ............................... G09G 3/36 |
| 9422889 | 10/1994 | WIPO ............................. C97H 21/00 |

OTHER PUBLICATIONS

Patent Abstracts of Japan, vol. 16, No. 472 (E–1272), Sep. 30, 1992.

Sensor and Actuators A, vol. 43, 1994, pp. 296–301, XP000567518, Kakerow et al, "A Monolithic Sensor Array of Individually Addressable Microelectrodes".

Sensors and Actuators B, vol. 19, Apr. 1994, pp. 675–677, XP000449927, Fiaccabrino et al, "Array of Individually Addressable Microelectrodes".

Semiconductor FabTech, pp. 289–295, John Franka et al., "Technology: Present and Future".

R. Kakerow et al; "Sensors and Actuators A Physical"; Jun. 7–10, 1993; pp. 296–301; Yokohama, Japan vol. A43 Nos. 1–3.

G.C. Fiaccabrino et al; "Sensors and Actuators B Chemical"; vol. B19; Apr. 1994; Budapest, Hungary; pp. 675–677.

T. Hermes et al; "Sensors and Actuators"; Jul. 1994; vol. B21; pp. 33–37 Lausanne, CH.

John Franka et al' "Technology: Present and Future"; Advnaced.

Packaging Technology; Austin, Texas; pp. 289–290, 293–295;published date unknown.

Caillat e3t al; "Fluxless Flip–Chip Technology"; Grenoble Cedex–France; pp. 1–5; publication date unknown.

*Primary Examiner*—Stephone B. Allen
*Attorney, Agent, or Firm*—Hayes, Soloway, Hennessey, Grossman & Hage PC

[57] ABSTRACT

Support comprising electrodes covered by a deposit and a system for reading this support. This support comprising a substrate (22) and electrodes (24) on this substrate, at least one of these electrodes being designed to be covered by a deposit capable of recognizing and capturing molecule-targets that are sensitive to a first light and that are capable of emitting a second light when they are excited by the first light. The substrate and electrodes are transparent to at least the first or the second light. The system comprises a light source (60) emitting the first light and means (62) of detecting the second light. Application to biological sensors.

23 Claims, 6 Drawing Sheets

U.S. PATENT DOCUMENTS

| | | | |
|---|---|---|---|
| 5,256,578 | 10/1993 | Corley et al. | 437/8 |
| 5,308,754 | 5/1994 | Kankare et al. | 435/7.4 |
| 5,384,028 | 1/1995 | Ito | 204/406 |
| 5,389,556 | 2/1995 | Rostoker et al. | 437/8 |
| 5,422,498 | 6/1995 | Nikawa et al. | 257/48 |
| 5,472,561 | 12/1995 | Williams et al. | 156/627.1 |
| 5,543,334 | 8/1996 | Yoshii et al. | 437/8 |
| 5,554,531 | 9/1996 | Zweig | 435/286.1 |
| 5,650,062 | 7/1997 | Ikeda et al. | 204/403 |
| 5,728,532 | 3/1998 | Ackley | 435/6 |
| 5,846,842 | 12/1998 | Herron et al. | 436/518 |

ELECTRODE SUPPORT COMPRISING AT LEAST ONE ELECTRODE COVERED BY A DEPOSIT AND SYSTEM FOR READING THIS SUPPORT

TECHNICAL DOMAIN

This invention relates to an electrode support comprising at least one electrode covered by a deposit and a system for reading this support.

The invention is particularly applicable to the manufacture of sensors or other miniaturized sensitive elements in which chips have to be made with a large number of electrodes.

These electrodes must be coated by appropriate materials to make them capable of carrying out their specific functions in the sensor or the sensitive element.

For example, the invention is applicable to the manufacture of miniaturized elements such as "biochips" which are chips comprising an electric circuit part formed on a substrate such as a field of electrodes, and a biological part formed on the surface of the chip.

In this example, chemical compounds compatible with the biological products have to be deposited selectively on the electrodes.

STATE OF PRIOR ART

Electrode supports made of silicon are known and comprise active elements enabling electrochemical deposition on these electrodes by appropriate addressing.

Furthermore, the associated systems that make it possible to read what is deposited on the electrodes use a light source capable of illuminating the top surface of electrodes, and light detection means placed facing electrodes and associated with the said optical means.

The main problem that arises with this type of structure is their cost.

All this is illustrated schematically by FIGS. 1 to 3 in the attached drawings.

FIG. 1 shows a substrate 2, for example made of silicon.

The surface of this substrate 2 is made functional by grafting of molecules-sensors.

Furthermore, this surface is made selectively functional by selective addressing of one electrode among a number of independent electrodes E1, E2, E3 and E4, for example electrode E2, the other electrodes not being selected.

Addressing an electrode corresponds to applying a voltage different from the reference voltage of a bath (not shown) to the electrode, the molecule-sensors being diluted in the bath.

This voltage different from the reference voltage must be sufficiently high to cause either an electrodeposition phenomenon (if polypyrrol or polyaniline type conductor polymers are used), or an irreversible transfer of charges (in the case of a covalent grafting reaction).

Addressing is achieved by creating a control circuit 4 on the surface of the substrate 2 on which the electrodes are placed.

In the example shown in FIG. 1, this control circuit 4 is a demultiplexer that receives high order data and low order data through electric lines 6 and 8 and which controls the four independent electrodes E1, E2, E3 and E4 through four transistors T1, T2, T3 and T4 respectively.

FIG. 1 also shows a line 9 that is used to apply a voltage V to demultiplexer 4 output transistor sources.

This voltage V is used to polarize electrodes selected using this demultiplexer 4.

These electrodes (or more precisely the material deposited on these electrodes) are read optically:

either by using an optical system such as that shown schematically in FIG. 2, or by incorporating photodetectors on substrate 2 as illustrated schematically in FIG. 3.

FIG. 2 shows a schematic and partial cross-section through substrate 2, with only two of electrodes E1 to E4, for example electrode E1 and electrode E2.

These electrodes E1 to E4 support all molecules-sensors 10.

After the electrochemical deposition step, the support with the electrodes is covered by an analyte containing molecule-targets suitable for being hybridized on some molecule-sensors.

The hybridizing circuit is then read either directly in the presence of the analyte or after the analyte has been eliminated as in the example shown in FIGS. 2 and 3.

Thus some of these molecule-sensors, for example those for electrode E2, are hybridized at DNA branches 12 whereas the others are not.

These DNA branches 12 are marked by a fluorescent marking product such that, when the DNA branches thus marked are illuminated by light with wave length $\lambda 1$ from a light source not shown, these marked branches emit light with another wave length $\lambda 2$.

A lens 14, fitted with an optical filter 16 capable of stopping light with wave length $\lambda 1$ and allowing light with wave length $\lambda 2$ to pass, is placed above the surface of substrate 2 facing the electrodes.

Detection means 18, for example including charge coupled devices, are placed above the lens 14, this lens 14 thus being inserted between detection means 18 and the surface of substrate 2.

These detection means 18 detect light at wave length $\lambda 2$ which is focused on the charge coupled devices.

In the variant schematically and partially illustrated in FIG. 3, photodetectors 20 centered on wave length $\lambda 2$ are used, the photodetectors being integrated in substrate 2 and placed close to the electrodes.

As mentioned above, the main problems of systems like that illustrated schematically in FIGS. 1 to 3 is cost, namely:

the cost of the "biochip" made of silicon, the cost of detection either by an optical system (FIG. 2) or by integrated detectors (FIG. 3).

Furthermore, when reading is done in the presence of the analyte, the reading is disturbed by the presence of the analyte.

DESCRIPTION OF THE INVENTION

The purpose of this invention is to overcome the disadvantages mentioned above, by proposing to use a substrate and electrodes that are transparent to light that will excite marked DNA branches and/or the light emitted by these branches.

For example, the light source that emits this Light may be placed under the substrate such that detection means may be placed sufficiently close to electrodes so that there is no longer any need for the optical system (lens+filter), or vice versa.

More precisely, the purpose of this invention is an electrode support, this support comprising a substrate and electrodes that are formed on this substrate, at least one of these electrodes being designed to be covered by a deposit capable of recognizing and capturing molecule-targets that are sensitive to the first light and that are capable of emitting a second light distinct from the first light when these molecule-targets are excited by the first light, this support being characterized by the fact that the substrate and electrodes are transparent to at least the first or the second light.

The substrate and electrodes are transparent to the first light when the source of the first light is placed under the support, and they must be transparent to the second light when the detection means of the second light are placed under the support.

In order to simplify the optical elements necessary to illuminate the molecule-targets and to detect light emitted by them, it is advantageous to place the source and detection means on opposite sides of the support.

The choice of the various possible layouts depends on the applications of the support.

In the special case in which reading takes place in the presence of the analyte containing molecule-targets, detection means are advantageously placed adjacent to the rear surface of the support to avoid deterioration of the signal emitted by the molecule-targets due to the presence of the analyte (for example absorption/defocusing).

To keep the analyte in the support, the support may be in the form of a dish that could be closed by a strip that must be transparent to the source light when the source is place adjacent to the front surface of the support.

The invention thus reduces the cost of the support and the system for reading this support is simplified compared with prior art.

The substrate is preferably made of glass, in order to further reduce the cost of the support.

Electronic means may be integrated into the substrate.

According to a specific embodiment of the support according to the invention, these electronic means comprise an addressing circuit that is integrated in the substrate and is designed to control the electrodes either to perform a selective electrochemical deposition, or to control the hybridizing phenomenon.

These electronic means may also include heating means.

Instead of (or in addition to) the addressing circuit, the support according to the invention may also include a multiplexing circuit which is integrated in the substrate and is designed for multiplexing of signals addressed to the electrodes.

Preferably, the addressing circuit and/or the multiplexing circuit are made of amorphous silicon.

This also contributes to reducing the cost of the support.

According to a first specific embodiment of the invention, areas between electrodes include additional means for stopping the first light.

According to a second particular embodiment, areas between the electrodes comprise additional means for controlling the electrical potential close to the electrodes.

Additional means preferably include electrically conducting elements opaque to the first light, placed in areas between the electrodes and electrically insulated from these electrodes.

As a variant, the additional means may comprise electrically insulating elements opaque to the first light, placed in areas between the electrodes.

According to a specific embodiment of the invention, the support comprises a dish capable of containing an analyte containing molecule-targets.

This invention also relates to a system for reading the electrode support according to the invention, this reading system comprising:

a light source capable of emitting the first light to excite the molecule-targets, and means of detecting the second light.

According to a particular embodiment of the system according to the invention, the electrodes form a matrix and detection means comprise a matrix of detectors of the second light.

These detectors may advantageously be equipped with a filter capable of absorbing and reflecting the first light and allowing the second light to pass.

The pitch of the detector matrix may also be equal to the pitch of the electrode matrix, or less than this pitch.

Detection means may also be placed directly facing the electrodes sufficiently close to them to avoid the use of optical focusing means between the electrodes and the detection means.

As a variant, the detection means may be integrated in the substrate or placed under the substrate.

The light source capable of emitting the first light may be placed under the substrate.

Detection means may include detectors of the second light and means of focusing this light on these detectors, these focusing means being placed between these detectors and the electrodes.

For example, these focusing means may include a network of microlenses and/or a network of microdiaphragms that are beneficially placed on the support.

BRIEF DESCRIPTION OF THE FIGURES

This invention will be better understood by reading the description of example embodiments given below, which is given for guidance only and is in no way restrictive, with reference to the attached drawings in which.

DETAILED DESCRIPTION OF SPECIFIC EMBODIMENTS

Figure 1:
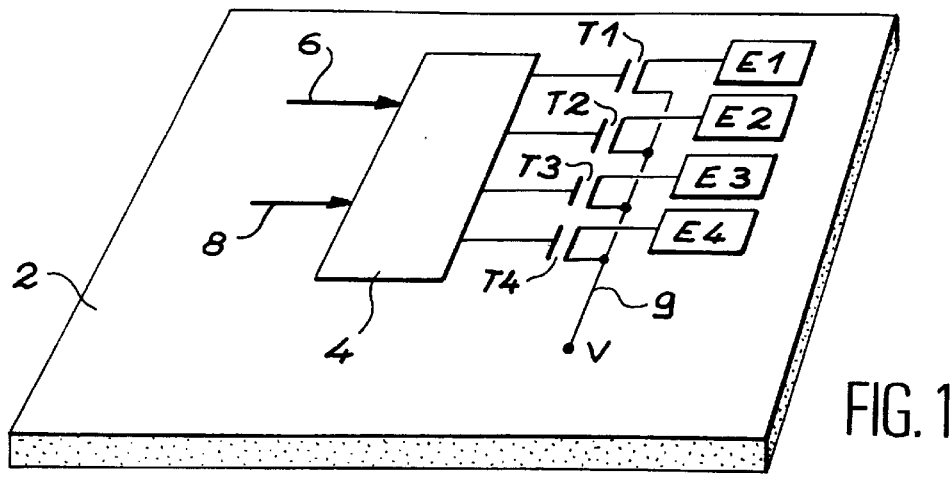
FIG. 1, already described, is a schematic perspective view of a known electrode support, FIG. 2, already described, is a schematic sectional view of a known electrode support, associated with a known system for reading electrodes, FIG. 3, already described, is a schematic sectional view of a known variant of the reading system in FIG. 2.
Figure 2:
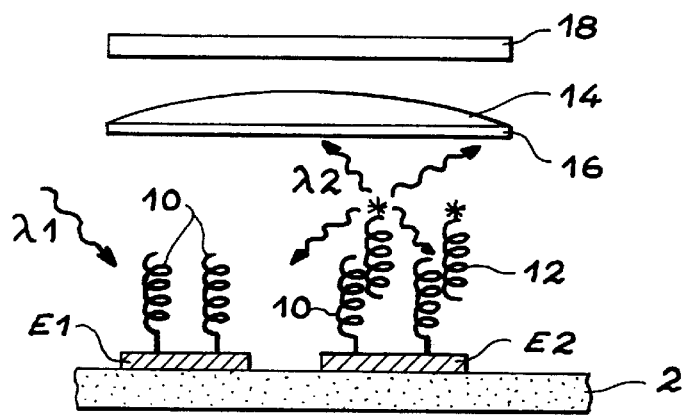
Figure 3:
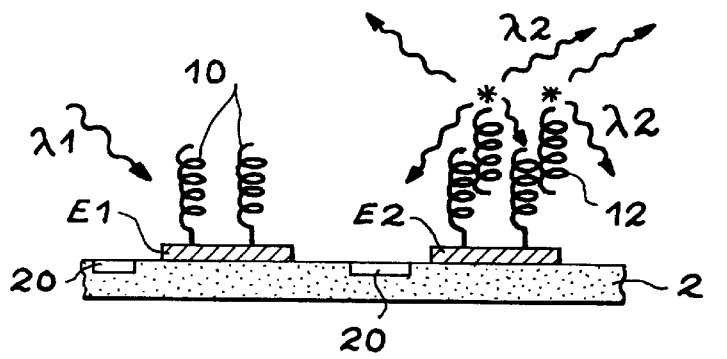
Figure 4:
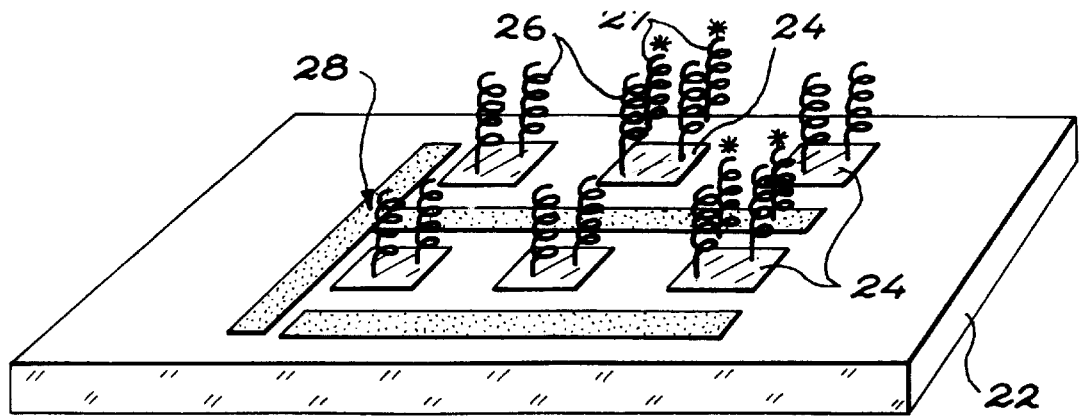
FIG. 4 is a schematic perspective view of a particular embodiment of the electrode support according to the invention.

The electrode support according to the invention, which is schematically shown in perspective in FIG. 4, comprises a glass substrate 22 and a matrix of electrodes 24 that are formed on the surface of this substrate 22.

Each electrode 24 is covered by an electrochemical deposit composed of molecule-sensors more simply referred to as "sensors".

These sensors are capable of recognizing and capturing molecule-targets that are sensitive to light with a wave length of $\lambda 1$.

("Light with a wave length of $\lambda$." means a spectral window containing $\lambda$).

All electrodes 24 carry sensors 26 on their surface, and some of these sensors have captured molecule-targets 27 whereas others have not.

When sensors receive light with wave length $\lambda 1$, the sensors that have captured molecule-targets, and only these sensors, emit light with a wave length of $\lambda 2$ through the molecule-targets, where $\lambda 2$ is different from $\lambda 1$ and can be detected as will be seen later.

The substrate 22 according to this invention is made of glass so that it is transparent to light with wave length $\lambda 1$ and all electrodes 24 are made of an electrically conducting material transparent to this light with wave length $\lambda 1$.

In the example shown in FIG. 4, the electrode support according to the invention also includes electronic means 28 that are integrated into the glass support 22 adjacent to the surface of this substrate which carries electrodes 24.

For example, these electronic means are made of amorphous silicon.

Furthermore, these electronic means consist of a circuit for addressing electrodes provided to enable the electrode functionalization step, in other words grafting of sensors.

This addressing circuit may comprise a multiplexing circuit depending on the complexity of the electrode matrix.

Figure 5:
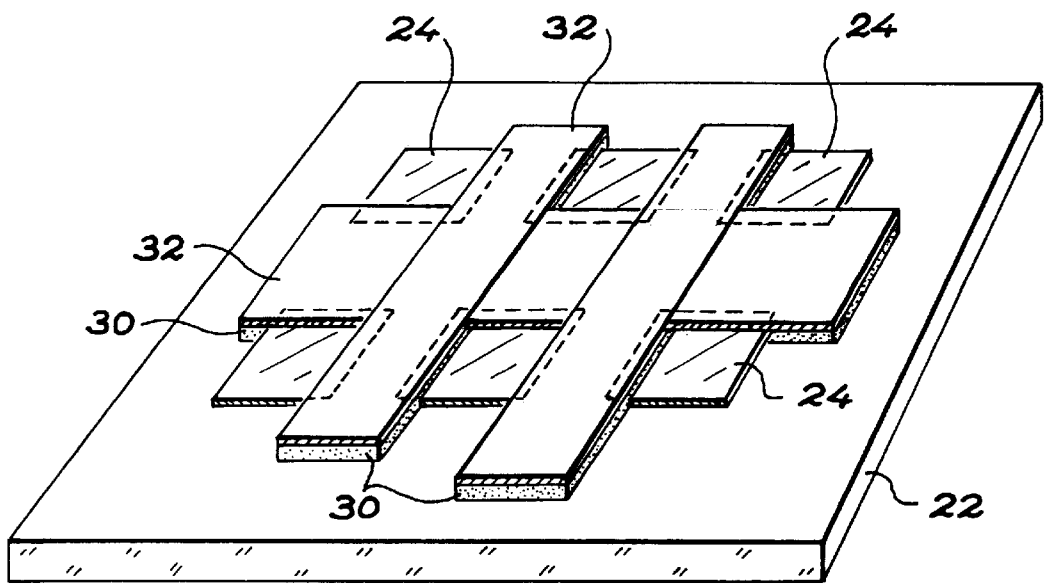
FIG. 5 is a schematic perspective view of an electrode support according to the invention.

The electrode support according to the invention, which is schematically shown in perspective in FIG. 5, is different from the support shown in FIG. 4 in that it also comprises electrically insulating elements 30 that are formed on the surface areas of substrate 22, which are included between electrodes 24.

Metallic layers 32 opaque to light with wave length $\lambda 1$ are formed on these insulating elements 30, in order to stop this light.

Metallic layers 32 may also control the electrical potential close to the electrodes 24.

They may form one or several counter-electrodes.

They also optically block insensitive parts of the electrode support.

Optical blocking in this way is a good way of improving the signal/noise ratio when optically reading the matrix.

Figure 6:
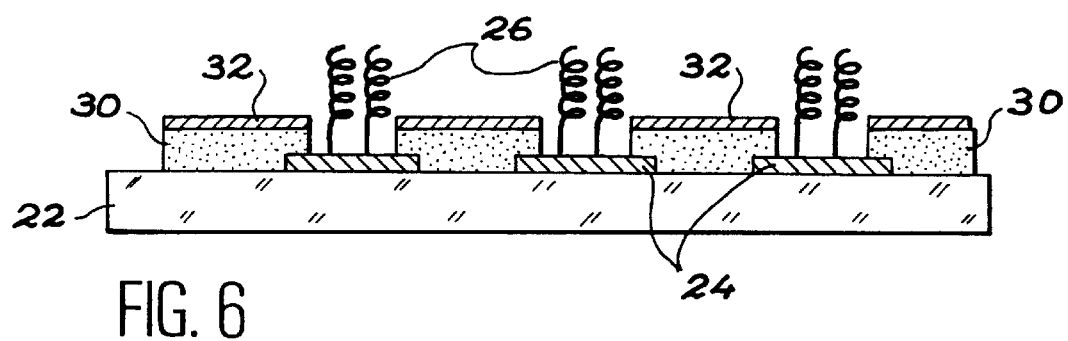
FIG. 6 is a schematic cross-sectional view of the support in FIG. 5, FIG. 7 schematically illustrates a method of addressing electrodes for a support according to the invention, FIG. 8 schematically illustrates an electrochemical deposit on electrodes of a support according to the invention, FIG. 9 schematically illustrates an electrochemical deposit on electrodes of another support according to the invention, FIG. 10 schematically illustrates an electrochemical deposit on the electrodes of another support according to the invention.

FIG. 6 is a schematic cross-sectional view of the electrode support in FIG. 5.

In one embodiment variant, the isolating elements 30 are formed on substrate 22.

These elements may advantageously be made from a material opaque to light with wave length $\lambda 1$, and also form optical blocking.

The following explains a method of addressing during the electrochemical deposition on electrodes such as those shown in FIGS. 4 and 5.

Figure 7:
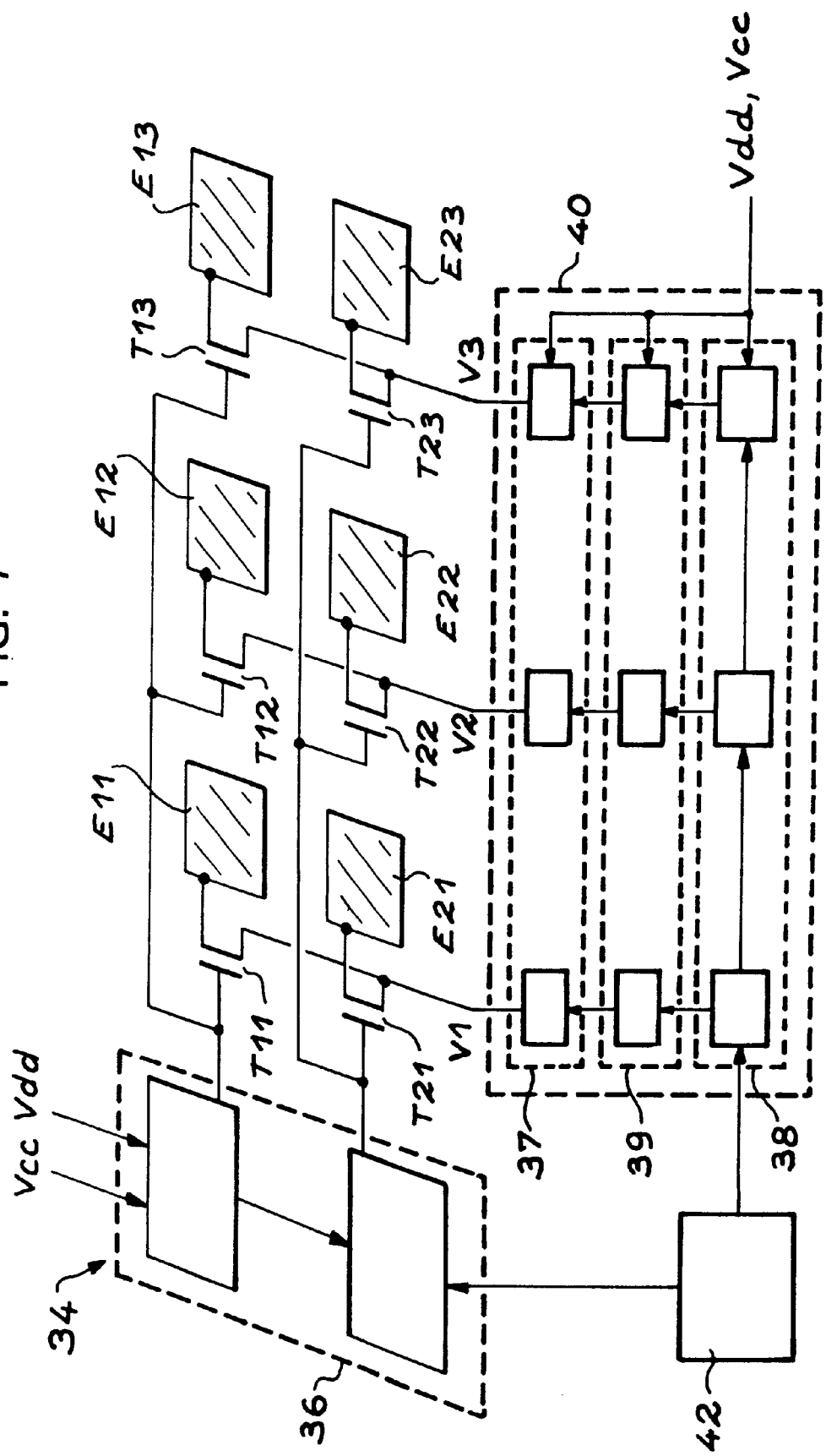

FIG. 7 shows a matrix with six electrodes.

These electrodes are referenced E11, E12 and E13 for the first row in the matrix, and E21, E22 and E23 for the second row in the matrix.

FIG. 7 also shows an electronic circuit 34 for controlling these electrodes.

This electronic circuit comprises an offset register 36 and another offset register 38.

This register 38 is associated with a "latch" type transfer register 39 combined with a "buffer" type amplification stage 37 with gain equal to 1, the assembly consisting of stage 37, register 38 and register 39 being identified as reference 40.

Each electrode Eij is associated with a transistor Tij, where index i may be any value between 1 and 2 and index j may be any value 1, 2 or 3.

The two registers 36 and 38 are controlled by a clock 42.

The register 36 comprises two outputs, one of which produces a signal S1 and the other a signal S2 for the two rows of the matrix respectively, through the transistors associated with it.

More precisely, transistors Tij are field effect transistors.

The drain of each transistor is connected to the corresponding electrode.

The transistor gates associated with the first row in the matrix are all connected to the first output of register 36 to receive signal S1.

The transistor gates associated with the second row in the matrix are all connected to the second output of register 36 to receive signal S2.

The sources of the two transistors associated with the first column of the electrode matrix are both connected -to a first output from the amplification stage 37, so that a controlled voltage reference V1 may be applied to them.

The sources of the two transistors associated with the second column of the electrode matrix are both connected to a second output from the amplification stage 37, so that a controlled voltage reference V2, possibly separate from V1, may be applied to them.

The sources of the two transistors associated with the third column of the electrode matrix are both connected to a third output from the amplification stage 37, so that a controlled voltage reference V3, possibly separate from V1 and V2, may be applied to them.

In FIG. 7, Vcc and Vdd represent the power supply voltages for registers 36 and 38.

Thus, electrodes can be adjusted sequentially, row by row using the matrix structure of these electrodes as was done in TFT matrices which are for use by the display.

Each of the voltages V1, V2 and v3 may be equal to a value that is less than the characteristic voltage threshold Vs of the selective functionalization (electrode not selected) or greater than this threshold (electrode selected).

The charge is only transferred when the selection signals S1, S2 exceed the transistor threshold, which is a condition for the transistors to be conducting ("on" state).

For example, transistor T11 is not selected when V1 is less than the threshold voltage Vs, although signal S1 is "on" and in this case there is no deposit on the corresponding electrode.

Transistor T11 is also not selected when V1 exceeds the voltage Vs but S1 is "off" in other words is less than the transistor threshold.

In the case in which S1 is "on" and V1 exceeds Vs at the same time, the deposit takes place on the electrode E11 associated with transistor T11.

This selection mode, although well known in display technology, is applied-directly here to make electrodes formed on the surface of a substrate such as substrate 22 selectively functional which, in the examples shown in FIGS. 4 to 6, forms a "biochip".

We will now describe how signals S1, S2, V1, V2 and V3 are produced.

These signals are obtained as described below, which is used for display units.

Signals S1 and S2 are output from the offset register 36 in FIG. 4.

Voltage signals V1, V2 and V3 are output from voltages Vcc and Vdd through assembly 40, an information transfer taking place at the same time while switching the offset register 36 and the parallel transfer register 39.

These functions can be achieved:
either by external electronics (movable connections on the electrodes),
or by making electronic circuits from amorphous silicon on the surface of the glass substrate 22 which carries the electrodes (the manufacturing process then being identical to the process for transistors associated with the electrodes matrix).

Note that the electronic circuit switching frequency may be low (about a few kHz) and therefore compatible with electronic mobility in amorphous silicon.

The manufacturing process mentioned above can be used for industrial treatment of glass plates about 500 µm thick and with sides about 500 mm, the manufacturing cost thus being lower than the manufacturing cost of electrode supports according to prior art.

We will now describe deposition methods.

Figure 8:
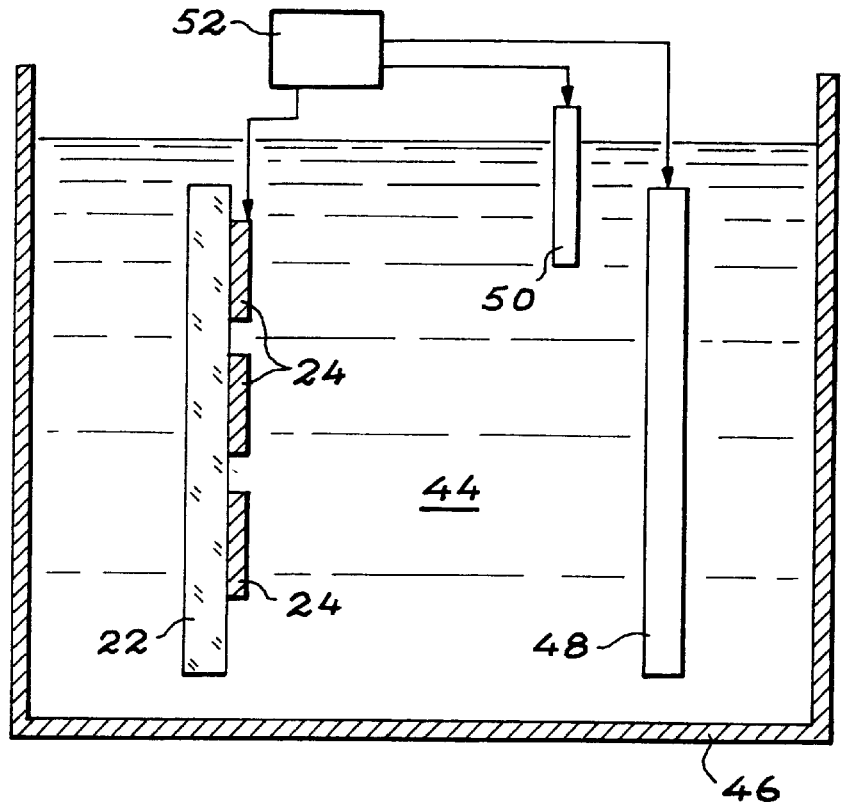

FIG. 8 shows the electrode support comprising a glass substrate 22 and electrodes 24.

This electrode support is dipped in a bath 44, for example a polypyrrole bath, contained in a receptacle 46.

There is a counter-electrode 48, also immersed in this bath 44, facing the electrode 24.

A reference electrode 50 can be used, which is also placed in the bath.

Electrodes 24 and electrode 48 and electrode 50 are connected to a potentiostat 52, to make selective deposits on electrodes 24.

Figure 9:
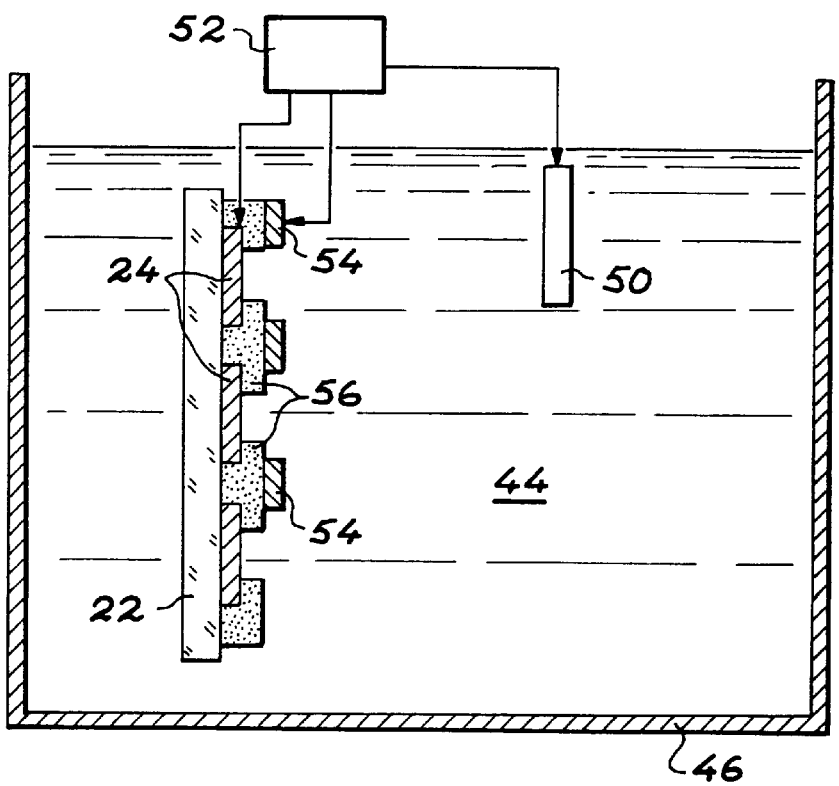

FIG. 9 schematically illustrates the possibility of making a counter-electrode on the substrate 22, for example in the form of a large number of small electrodes 54 associated with electrodes 24 respectively.

In this case, electrodes 54 are metallic layers formed on the insulating layers 56 respectively, themselves formed close to electrodes 24 respectively, as shown in FIG. 9.

During the deposit, there is a transfer of charges from each electrode 24 to the associated electrode 54.

Figure 10:
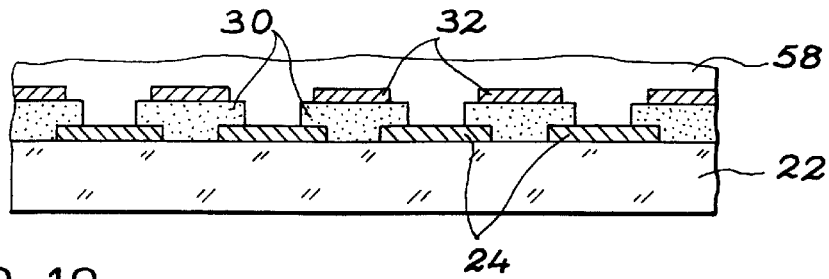

FIG. 10 schematically shows the possibility of using all metallic layers described with reference to FIGS. 5 and 6, as counter-electrodes.

This thus becomes a simplified deposition method limiting the necessary bath volume.

FIG. 10 shows electrodes 24 formed on the substrate 22, and metallic layers 32 formed on the insulating layers 30 respectively.

There is no reference electrode in the example shown in FIG. 10.

Note that the use of a reference electrode is particularly justified if the bath volume is large.

In FIG. 10, reference 58 represents the bath.

We will now describe the readout system for the electrode support in FIG. 4.

Figure 11:
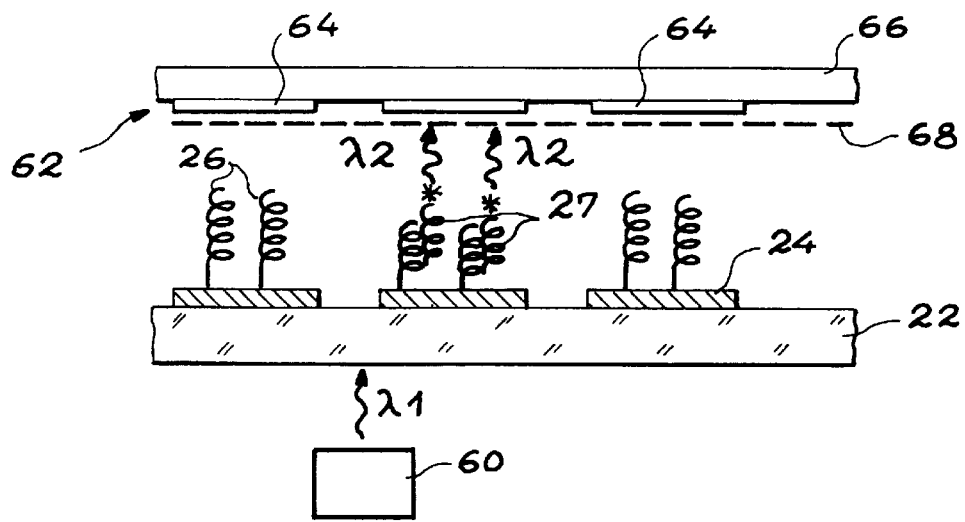
FIG. 11 is a schematic sectional view of a reading system according to the invention.

The explanation of how this support is read is given with reference to FIG. 11, which shows a cross-sectional view of the glass substrate 22 supporting electrodes 24 that are associated with molecule-sensors 26 respectively, some of which carry a marked molecule-target 27 whereas others do not.

The system for reading the electrode support 24 comprises a light source 60 designed to emit light at wave length $\lambda 1$.

This source 60 is placed under the glass substrate 22, as shown in FIG. 11.

Molecule-sensors that are marked, or more precisely that carry a marked molecule-target and which receive this light with wave length $\lambda 1$, in turn emit light with wave length $\lambda 2$.

The reading system also comprises means 62 of detecting light with wave length $\lambda 2$.

These detection means 62 comprise a matrix 64 on appropriate photodetectors (for example charge coupled detectors) (CCD).

This detectors matrix 64 is formed on an appropriate substrate 66.

Detection means 62 also comprise a selective filter 68 placed facing the charge coupled detectors and therefore inserted between these detectors and the electrodes 24 as shown in FIG. 11.

Taking account of the back lighting of substrate 22, detection means 62 can be positioned sufficiently close to the molecule-sensors so that there is no longer any need for optical focusing means between the electrodes and the photodetectors matrix.

A CMOS type photon detection matrix could be used instead of a matrix of charge coupled detectors (CCD).

The pitch of the photodetectors matrix 64 may be equal to the pitch of the electrodes matrix 24.

For example, the selective filter 68 could be made using thin layers (for example using multiple silicon oxide, titanium layers for which the refraction indices are different from each other).

The selective filter 68 allows light with wave length $\lambda 2$ to pass and absorbs or reflects light with wave length $\lambda 1$.

The use of layers 30 or 32 opaque at $\lambda 1$ is an advantageous embodiment of this invention, since there is less parasite light due to these opaque layers than in prior art.

As a variant, the pitch of the photodetectors may be less than pitch of the electrodes (and therefore at the same pitch as the molecule-sensors group) to avoid precise positioning of these photodetectors with respect to molecule-sensors.

Figure 12:
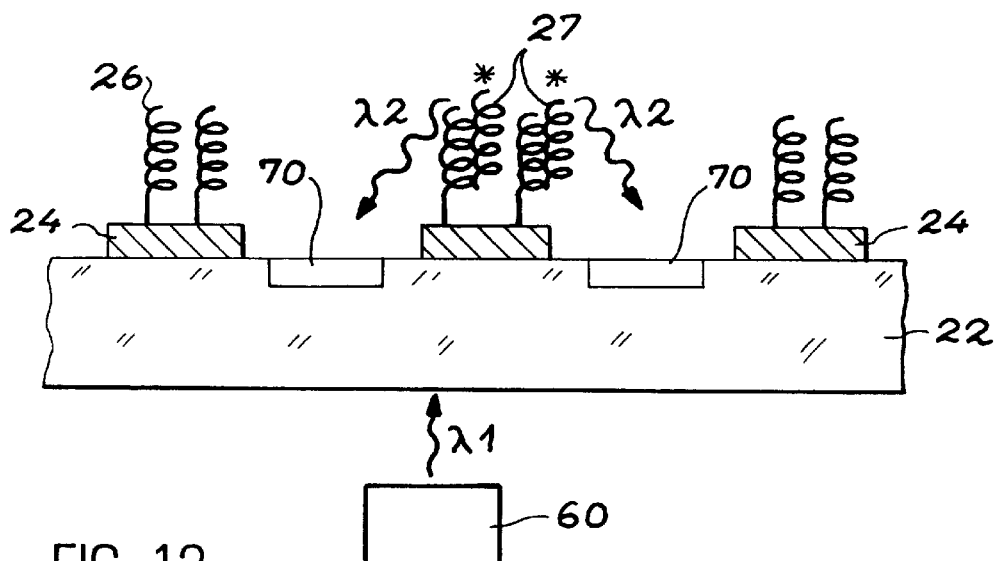
FIGS. 12 and 13 are schematic sectional views of other reading systems according to the invention.

FIG. 12 schematically illustrates the possibility of making the photodetectors matrix in the glass substrate, at the electrodes.

FIG. 12 shows this glass substrate 22 equipped with the electrodes matrix 24.

The photodetectors, which are then marked reference 70, are integrated into the glass substrate 22.

It still shows molecule-sensors 26 that are grafted onto electrodes 24, and some of which carry a marked molecule-target.

Figure 13:
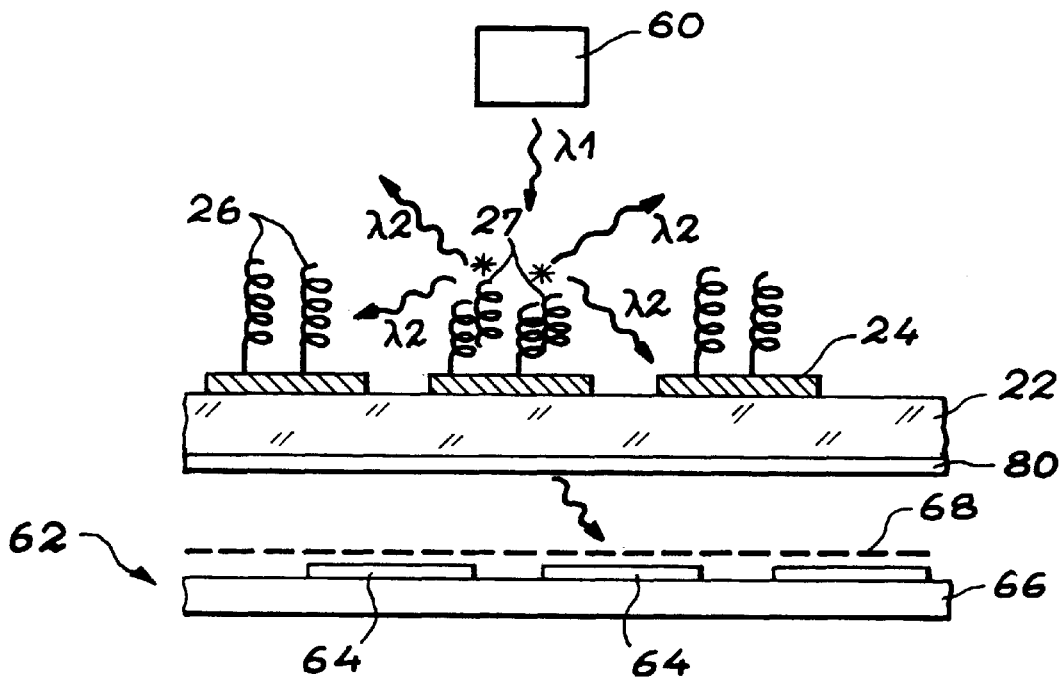

FIG. 13 schematically illustrates a variant of the invention.

In the-case shown in FIG. 13, the substrate 22 is transparent to light with wave length $\lambda 2$.

The source 60 is placed above the substrate 22, facing the electrodes 24.

The detection means 62 in FIG. 11 are also used in the case shown in FIG. 13, but they are p aced below the substrate 22 such that the matrix of photodetectors 64 receives light with wave length λ2.

In the case shown in FIG. 13, these detection means 62 also comprise focusing means 80 that are placed between the photodetectors and electrodes 24 and are provided to focus light with wave length λ2 onto the photodetectors.

These focusing means may include a network of microlenses or a network of microdiaphragms or both, these microlenses and/or microdiaphragms being formed on the rear surface of substrate 22.

In the examples of the invention shown schematically in FIGS. 4 to 13, it is assumed that hybridizing of molecule-targets on molecule-sensors is read after the analyte containing the molecule-targets has been eliminated.

Figure 14:
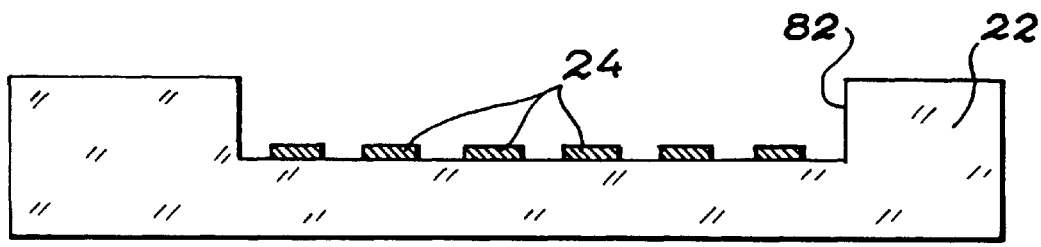
FIG. 14 is a schematic cross-sectional view of another support according to the invention.

FIG. 14 schematically illustrates the possibility of doing this reading in the presence of the analyte.

It can be seen that the substrate 22 then comprises a dish 82 that may contain the analyte containing the molecule-targets, at the bottom of which are located the electrodes 24.

The substrate may be formed from a single element (case of FIG. 14) or several elements which may be assembled to form the dish 82.

What is claimed is:

1. Electrode support, this support comprising a substrate (22) and electrodes (24) that are formed on this substrate, at least one of these electrodes being designed to be covered by a deposit capable of recognizing and capturing molecule-targets that are sensitive to a first light and that are capable of emitting a second light distinct from the first light when these molecule-targets are excited by the first light, this support being characterized by the fact that the substrate and electrodes are transparent to at least the first or the second light.

2. Support according to claim 1, in which the substrate is made of glass.

3. Support according to claim 1, in which the electronic means (28) are integrated into the substrate.

4. Support according to claim 3, in which these electronic means (28) comprise an addressing circuit that is integrated into the substrate and is designed to control the electrodes.

5. Support according to claim 1, also comprising a multiplexing circuit that is integrated into the substrate (22) and is designed for multiplexing signals addressed to electrodes (24).

6. Support according to claim 4, in which the circuit is made of amorphous silicon.

7. Support according to claim 1, in which the areas between the electrodes (24) comprise additional means (32) to stop the first light.

8. Support according to claim 1, in which the areas between the electrodes (24) comprise additional means (32) for controlling the electrical potential in the vicinity of electrodes.

9. Support according to claim 7, in which the additional means comprise electrically conducting elements (32) opaque to the first light, placed in the areas between the electrodes and electrically insulated from these electrodes.

10. Support according to claim 7, in which the additional means comprise electrically insulating elements opaque to the first light, placed in the areas between the electrodes.

11. Support according to claim 1, in which the support comprises a dish suitable for containing an analyte containing molecule-targets.

12. System for reading from the support according to claim 1, this reading system comprising:
   a light source (60) capable of emitting first light to excite molecule-targets, and
   means (62) of detecting the second light.

13. System according to claim 12, in which the electrodes (24) form a matrix and detection means comprise a matrix of detectors (64, 70) of the second light.

14. System according to claim 13, in which these detectors are fitted with a filter (68) capable of absorbing or reflecting the first light and allowing the second light to pass.

15. System according to claim 13, in which the pitch of the photodetectors matrix (64) is equal to the pitch of the electrodes matrix(24).

16. System according to claim 13, in which the pitch of the detectors matrix is less than the pitch of the electrodes matrix.

17. System according to claim 12, in which the detection means (62) are placed directly facing the electrodes, and sufficiently close to them to prevent the use of optical focusing means between the electrodes and detection means.

18. System according to claim 12, in which the detection means are integrated in the substrate (22).

19. System according to claim 12, in which the detection means (62) are placed under the substrate.

20. System according to claim 12, in which the light source (60) is placed under the substrate (22).

21. System according to claim 19, in which the detection means (62) comprise detectors (64) of the second light and means (80) of focusing this second light on these detectors, these focusing means being placed between these detectors and the electrodes.

22. Support according to claim 5, in which the circuit is made of amorphous silicon.

23. Support according to claim 8, in which the additional means comprise electrically conducting elements (32) opaque to the first light, placed in areas between the electrodes and electrically insulated from these electrodes.

* * * * *